United States Patent [19]
Burnett et al.

[11] Patent Number: 4,592,890
[45] Date of Patent: Jun. 3, 1986

[54] DENTAL PROSTHESES ALLOY

[75] Inventors: Arthur P. Burnett; Wayne C. Bollinger, both of York, Pa.

[73] Assignee: Dentsply Research & Development Corp., Milford, Del.

[21] Appl. No.: 521,485

[22] Filed: Aug. 8, 1983

[51] Int. Cl.$^4$ .............................................. C22C 19/05
[52] U.S. Cl. .................................... 420/442; 433/207
[58] Field of Search ................ 420/442, 443, 445–453; 148/410, 427, 428; 433/207

[56] References Cited

U.S. PATENT DOCUMENTS

| | | |
|---|---|---|
| 1,942,150 | 1/1934 | Rohn . |
| 1,945,679 | 2/1934 | Corson . |
| 2,072,911 | 3/1937 | Touceda . |
| 2,089,587 | 8/1937 | Touceda . |
| 2,150,255 | 3/1939 | Touceda . |
| 2,621,122 | 12/1952 | Gresham et al. . |
| 2,631,095 | 3/1953 | Griffiths et al. . |
| 2,850,384 | 9/1958 | Starr . |
| 3,464,817 | 9/1969 | Griffiths . |
| 3,704,182 | 11/1972 | Griffiths . |
| 3,749,570 | 7/1973 | Lyon . |
| 3,753,800 | 8/1973 | Griffiths . |
| 3,914,867 | 10/1975 | Manning . |
| 4,014,691 | 3/1977 | Mohammed . |
| 4,049,427 | 9/1977 | Guerra . |
| 4,108,642 | 8/1978 | Chiaramonte . |
| 4,288,247 | 9/1981 | Shaw . |
| 4,292,076 | 9/1981 | Gigliotti et al. . |

FOREIGN PATENT DOCUMENTS

| | | |
|---|---|---|
| 62840 | 10/1938 | Czechoslovakia . |
| 404012 | 1/1934 | United Kingdom . |
| 1465157 | 2/1977 | United Kingdom . |
| 2038359 | 7/1980 | United Kingdom . |

OTHER PUBLICATIONS

"Recommended Procedures for Biobond ® Crown and Bridge Ceramic Bonding Alloy"; Copyright 1977, 1980 by Dentsply Int'l. Inc., York, Pennsylvania; pp. 1–2, 20–21.

"The Dentsply Biobond ® Technique"; Copyright 1979, 1982 by Dentsply Int'l. Inc., York, Pennsylvania; pp. 1–2, 8–21.

*Primary Examiner*—R. Dean
*Attorney, Agent, or Firm*—Edward J. Hanson, Jr.

[57] ABSTRACT

Disclosed is an alloy that is a combination by weight percent of 78 to 84 percent nickel, 11 to 15 percent chromium, 3 to 5 percent vanadium, and 1 to 2 percent beryllium. Any balance of other elements make up less than 7 percent with aluminum, manganese, silicon, tin, lanthanum, cerium, praseodymium, neodymium, samarium, gadolinium, molybdenum, niobium, tantalum, tungsten, titanium, iron, boron, and carbon specifically disclosed. The alloy is, in particular, a dental casting alloy or dental veneering alloy, and dental prostheses containing the alloy is a feature of the disclosure.

14 Claims, No Drawings

DENTAL PROSTHESES ALLOY

BACKGROUND OF THE INVENTION

This invention relates to alloys and especially to dental alloys for casting prostheses and in particular to the well-known nickel-beryllium system.

An example of a nickel-beryllium system of the type including chromium is shown in U.S. Pat. No. 3,704,182. This patent also refers to the use of vanadium. U.S. Pat. No. 3,704,182 is, however, a high beryllium alloy, i.e., 14 plus atomic percent beryllium, which is over 2 weight percent beryllium in the alloy system of his invention and would be over 2 weight percent in the alloy system of the present invention. The casting alloy of U.S. Pat. No. 3,074,182 is an extremely hard alloy which would not be suitable for making dental prostheses.

It has now been discovered that with the use of low beryllium and the amount of vanadium required by the present invention, a dental prostheses alloy is obtained, having substantial uniformity of grain size throughout the entire thickness of the prostheses, both in thin marginal areas and thick pontic areas. In addition, the alloy exhibits exceptional dental porcelain bonding properties and unusual freedom in time-temperature relationships during processing.

It is an object of the present invention to provide a nickel-based casting alloy that exhibits superior dental procelain bonding.

Another object of the present invention is to provide a dental casting alloy that is uniform in grain size throughout its cast mass.

It is a still further object of the present invention to provide a casting alloy suitable for use in forming dental prostheses, using essentially the procedures presently employed in forming such prostheses.

Yet another object of the present invention is the provision of a dental casting alloy, with procelain to metal bonding characteristics that are relatively insensitive to processing variables.

SUMMARY OF THE INVENTION

The present invention in one of its preferred aspects is a dental casting alloy consisting essentially in weight percent of about 78 to about 84 percent nickel (Ni), about 11 to about 15 percent chromium (Cr), about 3 to about 5 percent vanadium (V), and about 1 to about 2 percent beryllium (Be). Any balance of the dental casting alloy is of essentially additional elements by weight percent of 0 to about 3 percent of an element chosen from the group consisting of aluminum (Al), manganese (Mn), silicon (Si), tin (Sn), and the rare earths lanthanum (La), cerium (Ce), praseodymium (Pr), neodymium (Nd), samarium (Sm), and gadolinium (Gd); 0 to about 7 percent molybdenum (Mo), niobium (Nb), tantalum (Ta), tungsten (W), and titanium (Ti); 0 to about 2 percent iron (Fe); 0 to about 1 percent boron (B); and 0 to about 0.8 percent carbon (C). Each of the named additional elements is present individually or in combination with any other named additional element within the ranges specified and with incidental impurities, all not exceeding about 7 percent.

By another aspect of the invention, a dental prostheses formed of the dental casting alloy described above is provided and preferably a dental porcelain is permanently adhered to the dental casting alloy.

DESCRIPTION OF THE PREFERRED EMBODIMENT

The present invention in its preferred embodiment is an alloy particularly suitable for use in making dental prostheses and the like that is comprised of four essential elements in substantially critical proportions. The critical elements and substantially critical proportions are, on the basis of weight percent: nickel 78 to 84 percent; chromium 11 to 15 percent; vanadium 3 to 5 percent; and beryllium 1 to 2 percent. A dental casting alloy having the essential elements in the substantially critical amounts provides the superior properties that will be discussed below.

In addition to the essential elements just mentioned, the dental casting alloy may contain additional materials which would make up the balance of the alloy composition and constitute essentially additional elements which are preferably the elements in the weight percent of: 0 to 3 percent of an element chosen from the group consisting of aluminum, manganese, silicon, tin, and the rare earths lanthanum, cerium, praseodymium, neodymium, samarium, and gadolinium; 0 to 7 percent molybdenum, niobium, tantalum, tungsten, and titanium; 0 to 2 percent iron; 0 to 1 percent boron; and 0 to 0.8 percent carbon. Each of the named additional elements may be present individually or in combination with another named additional element within the range as specified and with incidental impurities, all together not exceeding approximately 7 percent. In other words by way of example, the alloy composition may contain a mixture of the rare earths in mixture with any combination of aluminum, manganese, silicon, and tin, as long as the combination does not exceed 3 percent, and these may be in addition to other recited elements in the additional element group as long as the overall combination does not exceed the 7 percent limit when any and all inherent impurities are also counted within the 7 percent.

Preferably, the essential elements are present in weight percentages of 78 to 83 percent nickel, 12 to 15 percent chromium, 3.5 to 4.5 percent vanadium, and 1.65 to 1.95 percent beryllium.

As already stated, the dental alloy is preferably formed into a dental prostheses and preferably one formed in the shape of a tooth or a plurality of teeth and or supporting portions, with at least one of the teeth, if not more than one, being coated with a procelain facing which permanently adheres to the alloy.

The compositions of the present invention all employ nickel-chromium compositions for their generally recognized ability to give excellent corrosion resistance necessary for prolonged use in the environment of the human mouth. The beryllium is believed to function in the combination of the present invention to significantly lower the melting range of the alloys while improving melt fluidity and castability. The chromium, beryllium, and vanadium all are believed to function in combination, in the preferred ratios of use given, to serve to reduce the thermal expansion of the alloys from that of nickel to the range desired for compatibility with dental procelain.

Carbon and/or boron may be added within the recited parameters for further adjustment of the alloy melting characteristics when desired and when this is done, it is frequently desirable to add strong carbide or boride formers such as molybdenum, niobium, tantalum, or titanium. The additions in proper recited proportions can also be formulated to serve to harden and strengthen the alloy and can offer advantageous ways to reduce the thermal expansion of the alloy.

The addition of tin and aluminum are believed to modify the melting range of the alloy and improve castability, though they may tend to undesirably increase thermal expansion of the alloy.

When the alloys of this invention are used as the substructure for dental procelains, the oxidation characteristics of the alloy are preferably controlled through the alloy composition in combination with heat treatment, chemical surface treatment, and/or mechanical surface treatment to insure the alloy surface is chemically compatible with the procelain to effect a stable bonding of the two materials. All the forementioned elements can potentially influence the bonding mechanisms in apparently both positive and negative ways, depending upon factors other than merely alloy composition. It is for this reason that for some alloys of this invention, and dependent upon the heat treatment and surface preparation used; the addition of highly oxidizable elements, such as iron, manganese, and the rare earths can benefit the integrity of the procelain to metal bond, though the mechanisms by which they can improve bonding are not well understood.

OPERATION

The alloys of this invention are based upon the nickel, chromium, vanadium, beryllium quaternary alloy sysitem. They are alloyable using generally accepted air melting foundry practice, though vacuum melting can be employed and, during air melting, an inert gas cover can be desirable. It is preferred that the beryllium be added to the melt in the form of a nickel-beryllium or nickel-chromium-beryllium master alloy. Vanadium may be added by using either a nickel-vanadium master alloy or elemental vanadium. Any other additions of addition elements are generally made in order of increasing risk of loss due to oxidation or volatilization.

In a preferred production procedure, the alloy is prepared by forming a melt of nickel, adding to the melt a nickel-chromium-beryllium master alloy, and then adding vanadium to this as well as any other intended ingredients as specified above. Then this alloy may be cast into ingots which will be remelted for the casting of dental metal substructures or prosthetic devices. The dental casting is produced by conventional lost wax investment casting techniques routinely used in commercial dental laboratories.

In the preferred application, the cast dental appliances are veneered with "dental porcelains" that are in common commercial use for the production of aesthetic fixed crown and bridge prostheses. Prior to the application of dental procelains, the cast substructures are heated treated to establish surface oxide conditions that optomize chemical bonding of the dental opaque procelains. The proper time, temperature, and atmospheric control will improve the bonding integrity, as known to those skilled in commercial dental laboratory procedures.

If the casting is a full metal crown, it is routinely only necessary to finish with conventional procedures of grinding and polishing as needed. If the casting is to be a denture or partial denture frame, it would again be finished in the usual manner, grinding, polishing, and etching as necessary. If a casting is to be used as an implant, the finishing and sterilization would be accomplished in the manner usually prescribed for such use.

When a dental procelain is to be applied, the surface will be ground, cleaned (for example, ultrasonically in alcohol or by sand blasting) and heat treated to oxidize the surface as necessary. Various other additional procedures may also be used depending on whether or not soldering will be necessary and particular applications of use. The dental procelain is conventionally applied in several layers of varying compositions and shades. Usually the initial layers are dental opaquing procelains and then there is a middle dental body porcelain and/or stains and then a covering glaze. The layers are conventionally applied by brushing or spatula using hand techniques. Each individual layer is usually fired and appropriate tooth anatomy is carved in each layer. The firing temperatures are conventionally in the range of 1100° F. to 1900° F. Finally, the exposed metal casting receives a final polishing.

All percentages in this patent application are weight percents based on 100 percent of the final alloy composition except where clearly indicated as percents of additive combinations as is indicated in Example 1 for the master alloy of nickel and master alloy of vanadium.

The invention is further illustrated by the following exampls:

EXAMPLE I

An alloy was prepared to contain 12.5 percent chromium, 1.9 percent beryllium, 4.0 percent vanadium, with the balance essentially nickel. This alloy was prepared by induction melting in an alumina crucible under a cover of argon gas. The nickel charge was melted, then the beryllium addition was made from a master alloy of nickel containing 2.5 weight percent beryllium and 12 weight percent chromium. The vanadium was then added from a master alloy of vanadium containing 33 percent nickel. The balance of the chromium was added as elemental chromium. This alloy was poured at approximately 2750° F. into 300° F. graphite bar molds then cut into approximately 5 gram ingots for remelting for casting of dental prostheses and test samples.

The alloy ingots were remelted by gas-oxygen torch heating and induction melting equipment common to dental laboratory practice and cast into commercially available dental phosphate bonded investments to produce three-unit bridge dental prostheses and test samples for evaluation of physical and mechanical properties of the alloy as described in the following tests:

Test 1

Microhardness measurements on metallographically finished samples in the as cast condition showed the alloy to be 310 $HV_{1K}$ using a Tukon microhardness tester without significant variation in hardness between thick and thin sections. Thick sections were as much as 6 mm. thick and thin sections were as thin as 0.5 mm.

Test 2

Tensile samples as described in ISO/ADA specification #14, dated Apr. 15, 1982, were prepared and tested in the as cast condition to show that the alloy has more than adequate strength and ductility for use in a dental prosthetic device. Typical Properties determined were as follows:

| | |
|---|---|
| Ultimate tensile strength | 130,000 psi |
| 0.2 percent offset tensile yield strength | 85,000 psi |

| | |
|---|---|
| -continued | |
| Elongation: | 9% in 1 cm. |

Test 3

Dilatometric measurements made using a Theta recording dilatometer showed the alloy to have a coefficient of thermal expansion over the temperature range of 25° C. to 500° C. of $14 \times 10^{-6} C^{-1}$.

Test 4

Differential thermal analysis done on a Tracor/Stone thermal analyzer showed the solidus temperature of the alloy to be 2120° F. Metallographic analysis of samples quenched from 2050° F. confirmed the solidus to be in excess of that temperature and lower than 2150° F.

Test 5

Cast alloy samples were metallographically prepared. Samples of about 1 cm.$^2$ and approximately 1 mm. thick were heat treated over a variety of times, temperatures, and atmospheres in a standard laboratory vacuum procelain firing furnace as indicated in the following table:

SCHEDULE OF SAMPLE PREPARATION CONDITIONS
PRIOR TO OPAQUE APPLICATION
A - air fired
V - vacuum fired

| | | Temperature (°F.) | | | | | | | |
|---|---|---|---|---|---|---|---|---|---|
| | | 1200 | 1400 | 1500 | 1600 | 1700 | 1740 | 1780 | 1200 to 1800 | 1200 to 1850 |
| Hold Time | 0 | | | | | | | | V | V |
| At Temp. | 5 | V | | V | | | V | | V | |
| Indicated | 10 | A,V | V | | A | V | A,V | V | | V |
| (0 to 15 Min.) | 15 | | | | | | V | | | |

The heat treated samples were coated with a dental opaquing procelain as would be done in usual bridge fabrication procedures, and subsequently subjected to the porcelain firing cycles common to the construction of veneered dental protheses.

The completed samples were mechanically impacted until failure of the opaque, then examined by scanning electron microscopy and energy dispersive X-ray analysis. The fracture was predominantly outside the metal-procelain interface. The failed samples showed extensive opaque was left on the metal surface and that the alloy exhibited greatest retention of the opaque in regions of the microstructure that were vanadium rich as determined by energy dispersive X-ray microanalysis. This is indicative of vanadium contributing to the procelain to metal bond.

Test 6

Three unit cast bridges of the alloy were prepared to receive procelain using usual dental laboratory procedures per a method described in the metal preparation section of "Recommended Procedures for BI-OBOND ® Crown and Bridge Ceramic Bonding Alloy," Dentsply International Inc.: Copyright 1980. The bridges were heat treated in vacuum for from five minutes to ten minutes at temperatures ranging from 1700° F. to 1780° F. in a dental laboratory vacuum procelain firing furnace. Commercially available SHADEMATE ™ opaque dental feldspathic procelain, a product of Dentsply International Inc., was applied and fired to the casting after it was oxidized by the heat treatment and subsequent cool down in air. The bridges were completed with a commercial dental procelain, BI-OBOND ® procelain, a product of Dentsply International Inc. using standard dental laboratory procedures. See "The Dentsply Biobond ® Technique," Copyright 1979 and 1982, Dentsply International Inc. The bridges thus produced were clinically acceptable dental prosthetic devices that visually exhibited good fit to the dies used in their preparation.

Test 7

Three-unit bridges were made by several dental labs using the alloy of Example 1 and their usual practices. Approximately thirty of these bridges were checked by visual observation: The shade of the procelain was unaffected by the alloy; and the restorations were free from any objectionable dark line at the procelain to metal interface.

The bridges were intentionally failed by the thermal shock of plunging them into room temperature water from a temperature of 950° C. In each bridge the fracture was predominantly outside the metal-procelain interface to an extent indicative of exceptional procelain to metal bonding. Very little difference in appearance after failure demonstrated that the bonding characteristics were insensitive to heat treatment conditions over the wide range of times and temperatures employed.

Test 8

Metallographic examination was performed by scanning electron microscopy of sections of castings from the alloy of Example 1 and three commercially available alloys with similar nickel, chromium, and beryllium concentrations (Rexillium ®III, Litecast ®B, and Cospan ®13.5) but not containing vanadium.

The three commercial alloys were investment cast according to the manufacturer's instructions using standard dental laboratory methods. The alloy of the present invention was prepared as in Example 1. The patterns cast were 2.5 cm. long by 1.0 cm. wide and varied in thickness from 6 mm. to 1 mm. in 1 mm. steps. The size of the primary dendrites was measured along lines of a 10 mm. × 10 mm. grid overlayed on 4 × 5 inch photomicrographs taken at 500× of sections 1 mm., 3 mm., and 6 mm. thick. The following table shows the average grain size, standard deviation in grain size, and percent increase in grain size from the 1 mm. section for each of the four alloys.

| Sample | Average Grain Size (Micrometers) | Grain Size Standard Deviation (Micrometers) | % Increase from 1 mm. Section |
|---|---|---|---|
| 1 Alloy Example 1 | | | |

| Sample | Average Grain Size (Micrometers) | Grain Size Standard Deviation (Micrometers) | % Increase from 1 mm. Section |
|---|---|---|---|
| 1 mm. section | 22.0 | 14.0 | — |
| 3 mm. section | 29.9 | 18.7 | 36% |
| 6 mm. section | 37.5 | 20.3 | 70.5% |
| 2 Rexillium ® III | | | |
| 1 mm. section | 9.1 | 6.2 | — |
| 3 mm. section | 32.3 | 18.6 | 255% |
| 6 mm. section | 36.8 | 22.1 | 304% |
| 3 Litecast ® B | | | |
| 1 mm. section | 13.8 | 6.8 | — |
| 3 mm. section | 30.0 | 15.6 | 118% |
| 6 mm. section | 38.0 | 15.9 | 176% |
| 4 Cospan ® 13.5 | | | |
| 1 mm. section | 12.4 | 6.3 | — |
| 3 mm. section | 34.2 | 19.7 | 176% |
| 6 mm. section | 41.7 | 20.9 | 236% |

The above results revealed for the alloy of the present invention a microstructure that was essentially equiaxed and unusual in that the grain size of the primary dendrites showed unusually small variation in size with variations in section thickness of the castings. This condition was unanticipated but highly desirable as it contributes to obtaining uniform physical and mechanical properties throughout the casting.

While in accordance with the patent statutes what is at present considered to be the preferred embodiment of the invention has been described, it will be obvious to those skilled in the art that numerous changes and modifications may be made therein without departing from the invention, and it is therefore aimed in the appended claims to cover all such equivalent variations as fall within the true spirit and scope of the invention.

It is claimed:

1. An alloy composition consisting essentially of in weight percent about 78 to about 84 percent nickel, about 11 to about 15 percent chromium, about 3 to about 5 percent vanadium, and about 1 to about 2 percent beryllium.

2. The alloy of claim 1 wherein said alloy consisting essentially of additional elements in weight percent 0 to about 3 percent of an element chosen from the group consisting of aluminum, manganese, silicon, tin, and the rare earths: lanthanum, cerium, praseodymium, neodymium, samarium, and gadolinium; 0 to about 7 percent molybdenum, niobium, tantalum, tungsten and titanium; 0 to about 2 percent iron; 0 to about 1 percent boron; and 0 to about 0.8 percent carbon; each named additional element present individually or in combination with another named additional element within the ranges specified and with incidental impurities not exceeding about 7 percent.

3. The alloy of claim 1 wherein said alloy consisting essentially of in weight percent about 78 to about 83 percent nickel, about 12 to about 15 percent chromium, and 3.5 to about 4.5 percent vanadium, and about 1.65 to about 1.95 percent beryllium.

4. The alloy of claim 2 wherein said alloy consisting essentially of in weight percent about 78 to about 83 percent nickel, about 12 to about 15 percent chromium, about 3.5 to about 4.5 percent vanadium, and about 1.65 to about 1.95 percent beryllium with the additional elements and impurities being not more than about 5 percent.

5. A dental prostheses comprising an alloy consisting essentially of in weight percent of about 78 to about 84 percent nickel, about 11 to about 15 percent chromium, about 3 to about 5 percent vanadium, and about 1 to about 2 percent beryllium.

6. The dental prostheses of claim 5 wherein said alloy is at least in part formed into the shape of a tooth and coated with a procelain facing which permanently adheres to said alloy.

7. The dental prostheses of claim 6 wherein said alloy consisting essentially of in weight percent about 78 percent to about 83 percent nickel, about 12 to about 15 percent chromium, about 3.5 to about 4.5 percent vanadium, and about 1.65 to about 1.95 percent beryllium.

8. The dental prostheses of claim 7 wherein said alloy consisting essentially of additional elements in weight percent 0 to about 3 percent of an element chosen from the group consisting of aluminum, manganese, silicon, tin, and the rare earths lanthanum, cerium, praseodymium, neodymium, samarium and gadolinium; 0 to about 7 percent molybdenum, niobium, tantalum, tungsten and titanium; 0 to about 2 percent iron; 0 to about 1 percent boron; and 0 to about 0.8 percent carbon; each named additional element present individually or in combination with another named additional element within the ranges specified and with incidental impurities not exceeding about 5 percent.

9. An alloy particularly suitable for use in making dental prostheses and the like consisting essentially of in weight percent of about 78 to about 84 percent nickel, about 11 to about 15 percent chromium, about 3 to about 5 percent vanadium, and about 1 to about 2 percent beryllium.

10. The alloy of claim 9 as a dental casting alloy wherein said alloy consisting essentially in weight percent of:
about 78 to about 84 percent nickel, about 11 to about 15 percent chromium, about 3 to about 5 percent vanadium, and about 1 to about 2 percent beryllium, any balance being essentially additional elements 0 to about 3 percent of an element chosen from the group consisting of aluminum, manganese, silicon, tin, and the rare earths: lanthanum, cerium, praseodymium, neodymium, samarium and gadolinium; 0 to about 7 percent molybdenum, niobium, tantalum, tunsten, and titanium; 0 to about 2 percent iron; 0 to about 1 percent boron; and 0 to about 0.8 percent carbon; each named additional element present individually or in combination with any other named additional element within the ranges specified and with incidental impurities not exceeding about 7 percent.

11. The dental casting alloy of claim 10 wherein said alloy consisting essentially of in weight percent about 78 to 83 percent nickel, about 12 to about 15 percent chromium, about 3.5 to about 4.5 percent vanadium, and about 1.65 to about 1.95 percent beryllium with the additional elements and impurities being not more than about 5 percent.

12. The alloy of claim 9 as a dental veneering alloy wherein said alloy consisting essentially of additional elements in weight percent 0 to about 3 percent of an element chosen from the group consisting of aluminum, manganese, silicon, tin, and the rare earths: lanthanum, cerium, praseodymium, neodymium, samarium, and gadolinium; 0 to about 7 percent molybdenum, niobium, tantalum, tungsten and titanium; 0 to about 2 percent iron; 0 to about 1 percent boron; and 0 to about 0.8 percent carbon; each named additional element present individually or in combination with another named additional element within the ranges specified and with incidental impurities not exceeding about 7 percent.

13. The alloy of claim 9 as a dental veneering alloy wherein said alloy consisting essentially of in weight percent about 78 to about 83 percent nickel, about 12 to about 15 percent chromium, about 3.5 to about 4.5 percent vanadium, and about 1.65 to about 1.95 percent beryllium.

14. The alloy of claim 12 as a dental veneering alloy wherein said alloy consisting essentially of in weight percent about 78 to about 83 percent nickel, about 12 to about 15 percent chromium, about 3.5 to about 4.5 percent vanadium, and about 1.65 to about 1.95 percent beryllium with the additional elements and impurities being not more than about 5 percent.

* * * * *